United States Patent [19]
O'Neal et al.

[11] Patent Number: 5,654,255
[45] Date of Patent: Aug. 5, 1997

[54] PLANT GROWTH REGULATING COMPOSITIONS AND METHODS

[75] Inventors: Thomas D. O'Neal, Durham, N.C.; David E. Millhouse, Visalia, Calif.; Wilhelm Rademacher, Limburgerhof, Germany

[73] Assignee: BASF Corporation, Mount Olive, N.J.

[21] Appl. No.: 647,699

[22] Filed: May 14, 1996

Related U.S. Application Data

[62] Division of Ser. No. 464,221, Jun. 5, 1995, Pat. No. 5,627,134.

[51] Int. Cl.$^6$ ........................... A01N 43/40
[52] U.S. Cl. ............... 504/130; 504/118; 504/174; 504/177
[58] Field of Search ............... 504/130, 118, 504/174, 177; A01N 43/40

[56] References Cited

U.S. PATENT DOCUMENTS

| | | | |
|---|---|---|---|
| 4,637,828 | 1/1987 | Schülze et al. | 71/76 |
| 4,747,868 | 5/1988 | Schmierer et al. | 71/92 |
| 4,808,213 | 2/1989 | Schmierer et al. | 71/92 |
| 4,886,545 | 12/1989 | Peck et al. | 71/88 |

OTHER PUBLICATIONS

Steward and Krikorian, Plants, Chemicals and Growth, Cornell University, 1971.
Johnson and Sussex, "1L–myo–Inositol 1–Phosphate Synthase from Arabidopsis thaliana," 1995.
Wilkins, The physiology of plant growth and development, McGraw–Hill (1990).
Herdin, Paul A. and McCarthy, Jack C., "Effects of Kinetin and Onium Related Bioregulators on Agronomic Tratis Allelochemicals, and Protein of Cotton," Crop Science Res. Lab., Miss. State, as printed in AGRO, Photoactivated Azole Pesticides, Part II. Synthesis Miticidal Activity, #67 (1991).
Khoshkhoo, Nazrin, et al, "Effects of Bioregulators on the Terpenoid Aldehydes in Root–Knot Nematode Infected Cotton Plants," J. Agric. Food Chem. 1993, 41, 2442–2446.
Hood, L.R., "Multiple Plant Growth Regulator Use on Short Staple Cotton," Univ. of Arizona, Cotton Physiology Conference, 1994 Beltwide Cotton Conferences, p. 1274.
Hedin, Paul A., et al "Effects of Bioregulators on Flavonoids, Insect Resistance, and Yield of Seed Cototn, J. Agric. Food Chem." 1986, 36, 1055–1061.
Hdein, Paul A., "Effects of Kinetin Formulations on Allelochemicals and Agronomic Traits of Cotton", J. Agric. Food Chem. 1991, 39, 549–553.

*Primary Examiner*—Allen J. Robinson
*Attorney, Agent, or Firm*—Nixon & Vanderhye P.C.

[57] ABSTRACT

Plant growth regulator (PGR) compositions include a plant growth regulating effective mixture of (A) a N,N-dimethyl piperidinium salt (preferably, mepiquat chloride), (B) a hexitol (preferably, myo-inositol), and optionally (C) a compound which promotes cytokinesis in plant cells (i.e., a cytokinin). The hexitol and cytokinin are most preferably provided collectively in the composition by the presence of an effective amount of coconut milk. Synergistic results in terms of enhanced cotton lint yields are obtained by applying the PGR compositions of this invention to growing cotton plants.

16 Claims, No Drawings

PLANT GROWTH REGULATING COMPOSITIONS AND METHODS

This application is a divisional of U.S. application Ser. No. 08/464,221 filed on Jun. 5, 1995 now U.S. Pat. No. 5,627,134.

FILED OF THE INVENTION

The present invention relates to compositions for regulating plant growth which comprise an effective mixture of (A) N,N-dimethyl piperidinium salts, (B) a hexitol, and optionally (C) a compound which promotes cytokinesis in plant cells (i.e., a cytokinin), and to methods for regulating plant growth with these compositions. In a preferred form of the invention the myo-inositol and cytokinin (and possibly other active) components of the compositions may be provided by coconut milk.

BACKGROUND AND SUMMARY OF THE INVENTION

Plant growth regulators affect the physiology of plant growth and influence the natural rhythm of a plant. More specifically, plant growth regulators may, for example, reduce plant height, stimulate seed germination, induce flowering, darken leaf coloring, minimize lodging of cereals, slow grass growth on lawns, reduce boll rot and provide better boll retention in cotton.

The plant growth regulator (PGR) known trivially as mepiquat chloride is well known and has been combined with other plant growth regulators, including cytokinins, as disclosed in U.S. Pat. Nos. 4,886,545, 4,747,868 and 4,637,828 (the entire content of each being expressly incorporated hereinto by reference.).

The endosperm of coconut, *Cocos nucifera* (known as "coconut milk" in its liquid form) is known to contain hexitols (e.g., myo-inositol and scyllo-inositol) and cytokinins which promote plant growth. Wilkins, "The Physiology of Plant Growth and Development", Chapter 3, pp. 85–123 (1969), and Steward et al, "Plants, Chemicals and Growth", pp. 108–111 and 134–138 (1971).

According to the present invention, synergistic plant growth results have been obtained by applying to plants a PGR composition which includes a plant growth regulating effective mixture of (A) a N,N-dimethyl piperidinium salt (preferably mepiquat chloride), (B) a hexitol (myo-inositol), and optionally (C) a compound which promotes cytokinesis in plant cells (i.e., a cytokinin).

DETAILED DESCRIPTION OF THE PREFERRED EXEMPLARY EMBODIMENTS

As used herein, the term "agriculturally acceptable" includes agricultural, industrial and residential use.

As used herein, "plant growth regulator" or "regulation" includes the following plant response; inhibition of cell elongation, for example reduction in stem height and internodal distance, strengthening of the stem wall, thus increasing the resistance to lodging; compact growth in ornamentals for the economic production of improved quality plants; promotion of better fruiting; increasing the number of ovaries with a view to stepping up yield; promotion of senescence of the formation of tissue enabling fruit to absciss; defoliation of nursery and ornamental bushes and trees for mail-order business in the fall; defoliation of trees to interrupt parasitic chains of infection; hastening of ripening, with a view to programming the harvest by reducing the harvest to one to two pickings and interrupting the food-chain for injurious insects.

As used herein plant growth regulator compositions include both package and tank mix compositions.

The present invention comprises compositions which include an effective mixture of (A) a N,N-dimethyl piperidinium salt (preferably mepiquat chloride), (B) a hexitol (preferably myo-inositol), and optionally (C) a compound which promotes cytokinesis in plant cells (i.e., a cytokinin).

Preferred component (A) plant growth regulators include salts of the formula:

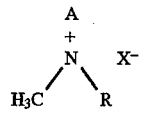

where R is methyl or ethyl; X is the anion of an inorganic or organic, but not phytotoxic acid, preferably bromide or chloride, and A is a chain of 4 or 5 methylene groups, which chain may be substituted by chloro, bromo, methyl, cholormethyl, bromomethyl, hydroxymethyl, and methylene, or which chain containing one or two double bonds, or A is the chain —$(CH_2)_n$—NH—, where n is 3 or 4, disclosed in U.S. Pat. No. 3,905,798 and hereby incorporated by reference.

Preferred examples of component (A) include 1,1-dimethyl-3,4-dehydro-piperidinium bromide, 4-chloro-1,1-dimethyl-piperidinium bromide, 1,1-dimethylhexahydropyridazinium bromide, 1,1-dimethylpiperidinium chloride and (2-chloroethyl) trimethylammonium chloride. The most preferred plant growth regulator is 1,1-dimethylpiperidinium chloride, also known as N,N-dimethylpiperidinium chloride or mepiquat chloride. This product is commercially available under the registered trademark Pix® (BASF AS, Germany). Component (A) will be present in the compositions of this invention in an amount between about 0.15 to about 100 grams active ingredient per acre per application (g ai/A/app), and sometimes between about 1 to about 20 g ai/A/app.

The compositions of this invention will necessarily include a plant growth stimulating effective amount of a hexitol. Preferred hexitols include inositols such as myo-inositol and scyllo-inositol, with myo-inositol being particularly preferred.

Virtually any compound which promotes cytokinesis in plant cells may be employed in the compositions of this invention. Preferred are substituted and unsubstituted kinetins, for example $N^6$-substituted adenines having either an alkyl or a purine substituent. Exemplary compounds within this claims include $N^6$-benzyl aminopurine, $N^6$-benzoylaminopurine, $N^6$-(2-naphthylamino)purine, $N^6$-(2-pyridylamino)purine, $N^6$-(2-thenylamino)purine, $N^6$-tetrahydrofurfurylaminopurine, and $N^6$-isopentenyladenine.

The hexitol and/or cytokinin will be present in the compositions in an amount of between about 0.1 to about 20 g ai/A/app, and preferably between about 1.0 to about 5.0 g ai/A/app.

The hexitol and cytokinin are most conveniently provided by mixing coconut milk with the N,N-dimethyl piperidinium salt. In this regard, coconut milk contains myo-inositol and other active ingredients. Thus, synergistic effects are shown when mepiquat chloride is mixed with coconut milk and applied to growing cotton plants. When employed in the compositions of this invention, the coconut milk may be any type commercially available and will preferably be present in an amount between about 20 ml to about 2000 ml per acre per application (ml/A/app), and more preferably between about 100 to about 500 ml/A/app, most preferably about 200 ml/A/app.

The compositions of this invention may be prepared, for example, by adding, in an any order, the various components of the compositions of the present invention. For example, one may start with a commercial formulation of mepiquat chloride, which is an aqueous concentrate containing 0.35 pounds per gallon of mepiquat chloride (4.2%) by weight. Thereafter, in any order, one mixes suitable amounts of component (B) and optionally component (C). In addition, any optional adjuvants or ingredients may then be mixed with the components. Water may be optionally employed in any amount desired.

The above plant growth regulator composition may then be dispersed in water and sprayed onto plants according to the method of the present invention. For example, spray volumes useful in the present invention range from about 0.25 gallons per acre to about 100 gallons per acre, and more preferably, from about 0.5 gallons per acre to about 40 gallons per acre.

While the ratios of the concentrations of the various components of the present invention are suggested herein, those skilled in the art will recognize that minor variations may be necessary to accommodate particular characteristics of acceptable plant growth regulators which may be employed in this invention. In general, for example, component (A) will contain from about 0.1 to about 98%, and preferably from about 0.5 to about 98% by weight of active ingredient.

The amount of water which is employed to prepare the concentrate or final application concentration, as in a spray, its adjusted as necessary. The concentrate and/or final composition may also be a dry formulation.

In addition to the above-described components, the compositions of the present invention may also include other ingredients or adjuvants commonly employed in the art.

Examples of such ingredients include drift control agents, defoaming agents, preservatives, surfactants, fertilizers, phytotoxicants, herbicides, pesticides, insecticides, fungicides, wetting agents, adherents, nematocides, bactercides, trace elements, synergists, antidotes, mixtures thereof and other such adjuvants well known in the plant growth regulator art.

The compositions of the present invention may be applied to above ground portions of the plants, to soil in which plants will be grown and/or to the seeds prior to planting. The application of liquid and particulate solid plant growth regulator compositions to above ground portions of plants may be carried out by conventional methods, for example, boom and hand application, including sprayers or dusters. The composition may be applied aerially as a spray, if desired. The mixtures of the present invention are preferably used in the form of aqueous solutions. The mixtures are applied in a conventional manner, for example, by spraying, atomizing, watering or disinfecting seed.

The compositions of the present invention may be applied for instance, in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting broadcasting or watering. The forms of application depend entirely on the purpose for which the compositions are being used. In any event, they should ensure a uniform distribution of the active ingredients in the composition.

For the preparation of solutions, emulsions pastes and oil dispersions to be sprayed direct, mineral oil fractions of medium to high boiling point, such as kerosene or diesel oil, further coal-tar oils, and the like, and oils of vegetable or animal origin, aliphatic, cyclic and aromatic hydrocarbons such as benzene, toluene, xylene, paraffin, tetrahydronaphthalene, alkylated naphthalenes and their derivatives such as lower (1–4 carbons) alcohols, chloroform, carbon tetrachloride cyclohexanol, cyclohexanone, chlorobenzene, isophorone, and the like, and strongly polar solvents such as dimethylformamide, dimethyl sulfoxide, N-methylpyrrolidone, water and the like are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means for wetting or dispersing agents, adherents or emulsifiers. Concentrates which are suitable for dilution with water may be prepared from active ingredients, wetting agents, adherents, emulsifying or dispersing agents and possibly solvent or oil.

Examples of surfactants include alkali metal, alkaline earth metal and ammonium salts of lignisulfonic acid, naphthalenesulfonic acids, phenosulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfates fatty alcohol glycol ether, condensation products of sulfonated naphthalene and naphthalene or naphthalenesulfonic acids with phenol and formaldehyde, polyoxyethylene octylphenol ethers, ethoxylated isoctylphenol, ethoxylated octylphenol and ethoxylated nonylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waster liquors, silicone based surfactants and methyl cellulose.

Powders, dusts and broadcasting agents may be prepared by mixing or grinding the active ingredients with a solid carrier.

Granules, for example, coated, impregnated or homogeneous granules, amy be prepared by bonding the active ingredients to solid carriers. Examples of solid carriers are mineral earths such as silicic acid, silica gels, silicates, talc, kaolin, Attaclay, limestone, lime, chalk, bole, loess, clay, domomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, and the like.

The following examples serve to illustrate the invention and should in no way be construed as limiting the scope thereof.

EXAMPLE

Compositions were prepared by mixing the ingredients and applying the mixture to 19 $m^2$ plots of cotton plants in three applications as low-rate multiple sprays beginning at mach-head square. The cotton plant height and yield of the cotton plants were determined. The results appear in Table I below with the data being presented as the treatment rate per application.

TABLE I

| Treatment | Rate (G AI/HA) | Plant Height[2] (cm) | Yield (kg lint/HA) |
|---|---|---|---|
| Untreated | | 91.5 | 1104 |
| Mepiquat Chloride[1] | 5 | 81.9 | 1125 |
| Myo-inositol @ 3 | 3 | 88.8 | 1173 |
| Myo-Inositol @ 6 | 6 | 90.1 | 1167 |
| Myo-Inositol @ 12 | 12 | 92.5 | 1172 |
| Invention Formulation 1: | | 90.2 | 1282 |
| Mepiquat Chloride | 5 | | |
| Myo-Inositol | 6 | | |
| Invention Formulation 2: | | 90.1 | 1253 |
| Mepiquat Chloride | 5 | | |
| Myo-Inositol | 6 | | |
| Coconut Milk | 500 ml | | |
| Invention Formulation 3: | | 88.7 | 1251 |
| Mepiquat Chloride | 5 | | |
| Coconut Milk | 500 ml | | |

Notes:
[1]BAS 083 30W (Pix ® PGR, BASF AG)
[2]No phytotoxicity observed.

As can be seen from the results in Table I above, the formulations of this invention containing a (A) a N,N-dimethyl piperidinium salt (preferably mepiquat chloride), (B) a hexitol (preferably myo-inositol), and optionally (C) a compound which promotes cytokinesis in plant cells (i.e., a cytokinin) synergistically promote increased cotton ling yields without exhibiting any phytotoxicity.

Therefore, while the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A cotton plant growth regulator (PGR) composition containing a cotton plant growth regulating synergistic effective amount of a mixture which comprises:

(A) between about 0.15 to about 100 grams active ingredient per acre per application of an N,N-dimethyl -piperidinium salt;

(B) a hexitol; and (C) a cytokinin, wherein (D) said hexitol and said cytokinin are present in said composition in an amount between about 0.1 to about 20 grams active ingredient per acre per application.

2. The PGR composition as in claim 1, wherein components (B) and (C) are collectively provided by the presence of an effective amount between about 100 to about 500 ml per acre per application of coconut milk.

3. The PGR composition as in claim 1 or 2, wherein the hexitol is myo-inositol.

4. The PGR composition as in claim 1, wherein the component (C) is present in an effective amount and is an adenine having an alkyl or a purine substituent at the N[6] position.

5. The PGR composition as in claim 4, wherein the N[6] substituent is selected from the group consisting of benzyl aminopurine, benzoylaminopurine, (2-naphthylamino) purine, (2-pyridylamino)purine, (2-thenylamino)purine, tetrahydrofurfurylaminopurine, and isopentenyladenine.

6. A cotton plant growth regulator (PGR) composition containing a cotton plant growth regulating synergistic effective amount of a mixture which comprises:

(A) between about 1 to about 20 grams active ingredient per acre per application of an N,N-dimethyl -piperidinium salt; and (B) between about 20 to about 2000 ml per acre per application of coconut milk.

7. The PGR composition as in claim 6, wherein said coconut milk is present in an amount between about 100 ml to about 500 ml per acre per application.

8. The PGR composition as in claim 6, wherein component (A) is mepiquat chloride.

9. A method of regulating cotton plant growth which comprises applying to growing cotton plants a composition which contains a cotton plant growth regulating synergistic effective amount of:

(A) between about 0.15 to about 100 grams active ingredient per acre per application of an N,N-dimethyl -piperidinium salt;

(B) a hexitol; and (C) a cytokinin, wherein (D) said hexitol and said cytokinin are present in said composition in an amount between about 0.1 to about 20 grams active ingredient per acre per application.

10. The method as in claim 9, wherein components (B) and (C) are collectively provided by the presence of an effective amount between about 100 to about 500 ml per acre per application of coconut milk.

11. The method as in claim 9 or 10, wherein the hexitol is myo-inositol.

12. The method as in claim 9, wherein component (C) is present in an effective amount and is an adenine having an alkyl or a purine substituent at the N[6] position.

13. The method as in claim 9, wherein component (C) is present in an effective amount and is an adenine having an alkyl or a purine substituent at the N[6] position.

14. The method as in claim 13, wherein the N[6] substituent is selected from the group consisting of benzyl aminopurine, benzoylaminopurine, (2-naphthylamino)purine, (2-pyridylamino)purine, (2-thenylamino)purine, tetrahydrofurfurylaminopurine, and isopentenyladenine.

15. A method of regulating cotton plant growth comprising applying to a growing cotton plant a cotton plant growth regulating synergistic effective amount of a mixture comprised of between about 0.1 to about 20 grams active ingredient per acre per application of an N,N-dimethyl-piperidinium salt, and between about 20 to about 2000 ml per acre per application of coconut milk.

16. The method as in claim 15, which comprises providing said coconut milk in said mixture in an amount sufficient to provide between 100 ml to about 500 ml per acre per application.

* * * * *